US005246761A

United States Patent [19]

Sasaki

[11] Patent Number: 5,246,761

[45] Date of Patent: Sep. 21, 1993

[54] BLADDER FOR AN ACCUMULATOR

[75] Inventor: Kenji Sasaki, Shizuoka, Japan

[73] Assignee: NOK Corporation, Tokyo, Japan

[21] Appl. No.: 764,678

[22] Filed: Sep. 25, 1991

[30] Foreign Application Priority Data

Sep. 26, 1990 [JP] Japan .................................... 2-25634

[51] Int. Cl.[5] ......................... B32B 3/00; B29D 22/00; A61F 5/44

[52] U.S. Cl. .................................... 428/156; 428/35.2; 428/35.4; 428/35.7; 428/36.6; 428/76; 428/172; 428/192; 428/213; 604/166; 604/317; 604/332; 206/438

[58] Field of Search ............... 428/156, 172, 212, 174, 428/35.2, 35.4, 35.7, 36.6, 35.9, 161, 192, 213, 68, 76, 99, 101; 604/317, 166, 408, 338, 332; 206/438

[56] References Cited

FOREIGN PATENT DOCUMENTS

3142390A1 5/1983 Fed. Rep. of Germany .
2453295 10/1980 France .
0360648 3/1990 France .
2102068A 1/1983 United Kingdom .

*Primary Examiner*—Donald J. Loney
*Attorney, Agent, or Firm*—Jacobson, Price, Holman & Stern

[57] ABSTRACT

A bladder (10) for an accumulator (20) has a hollow shell (21) formed of an elastic material layer (11), a gas-barrier layer (12) laminated thereon, and a central portion (11A). An elastic fitting portion is formed at an inner surface of a radially outward peripheral edge portion (11B) of the elastic material layer to be pressed radially outwardly towards the shell when the fitting portion (11A) is attached to the shell by an attaching element (22). The thickness of the bladder varies between the central and peripheral edge portions by being thinner proximate the central portion and thicker at a curved inversion portion (11C) between the intermediate portion and the outer peripheral edge portion to reduce rigidity at the intermediate portion and preventing lumping in the curved inversion portion.

9 Claims, 9 Drawing Sheets

BLADDER FOR AN ACCUMULATOR

BACKGROUND OF THE INVENTION

This invention relates to a bladder for an accumulator. More particularly, this invention relates to a bladder for an accumulator in which an intermediate portion of an elastic material layer is decreased in thickness so as to decrease its rigidity so that an outer surface portion of the elastic material layer at a curved or bent portion thereof can be prevented from expanding beyond the breaking expansion limit of a gas-barrier layer laminated thereon whereby buckling of the gas-barrier layer can be avoided.

PRIOR ART

A bladder for an accumulator is composed of an elastic material layer and a gas-barrier layer in a laminated condition, which have different elastic characteristics relative to each other. The bladder is arranged in an accumulator shell so as to define a gas chamber and a liquid chamber. When a liquid pressure in the liquid chamber decreases, a central portion of the bladder moves into the liquid chamber in a discharging direction. When the pressure in the liquid chamber increases, the central portion of the bladder moves into the gas chamber in a suction direction.

The conventional bladders for accumulators have substantially a constant or uniform thickness over their full range from their central portion to their peripheral edge portion so as to have a large rigidity. If the bladder is in non-load condition, the central portion of the bladder is inverted at its curved inversion area in the extending direction of its end edge so as to protrude into the gas chamber. Therefore, when the central portion of the bladder moves in the suction or discharging direction, the curved inversion area receives a lot of stress in such a way that an outer surface portion of the elastic material layer may expand at the curved inversion area beyond the breaking expansion limit of the gas-barrier layer. Further, the gas-barrier layer may buckle at its curved inversion area. As a result, the elastic material layer and the gas-barrier layer are sometimes broken. In particular, if the gas-barrier layer is made of a resin material having a small elasticity, the life time is shortened.

SUMMARY OF THE INVENTION

The object of the present invention is to provide a bladder for an accumulator in which an outer surface of the bladder can be prevented from expanding at its curved inversion area beyond the breaking expansion limit of a gas-barrier layer so as to avoid the gas-barrier layer buckling.

According to the present invention, a bladder for an accumulator including a shell comprises an elastic material layer, a gas-barrier layer laminated thereon, and an elastic fitting portion formed at a peripheral edge portion of the elastic material layer so as to be pressed onto an inner surface of the shell when the fitting portion is attached to the inner surface of the shell by means of an attaching element. The thickness of the elastic material layer decreases at an intermediate portion thereof and/or increases at a curved inversion portion thereof.

The outer surface portion of the elastic material layer can be prevented from expanding at its curved inversion area beyond the breaking expansion limit of the gas-barrier layer. In addition, buckling of the gas-barrier layer can be avoided at the curved inversion area. Accordingly, even if the gas-barrier layer is made of a resin material having a small elasticity, the bladder can have an excellent durability and a long life time.

BRIEF DESCRIPTION OF THE DRAWINGS

For a better understanding of the present invention, a detailed description will now be presented, by way of example with reference, to the drawings, wherein.

DETAILED DESCRIPTION OF PREFERRED EMBODIMENTS

THE FIRST EMBODIMENT

Figure 1:
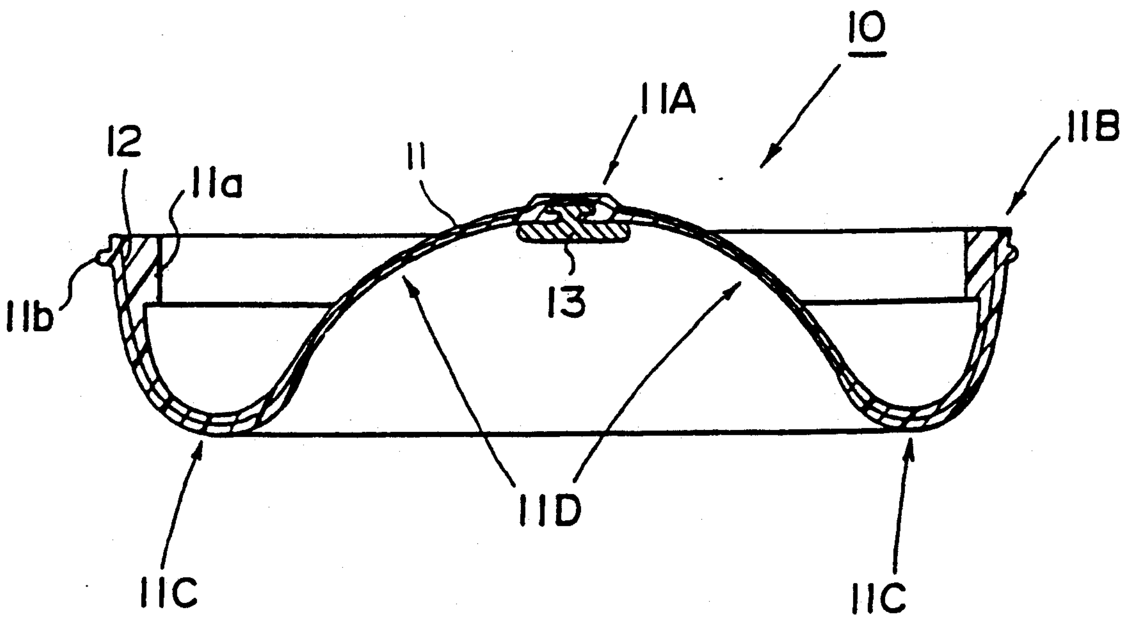
FIG. 1 is a cross sectional view showing a bladder for an accumulator according to a first embodiment of the present invention.
Figure 2:
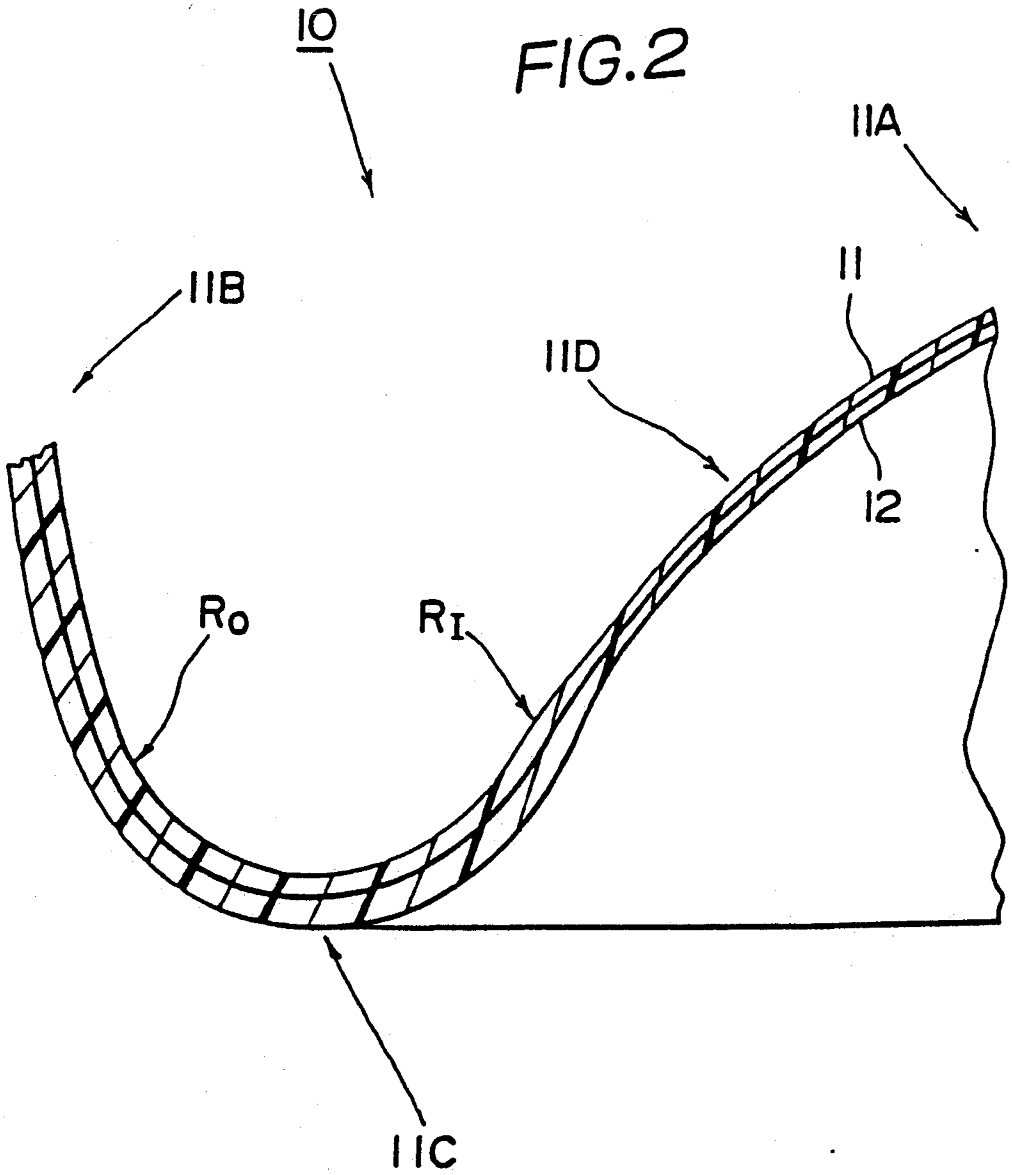
FIG. 2 is an enlarged cross sectional view showing a portion of the bladder shown in FIG. 1.
Figure 3:
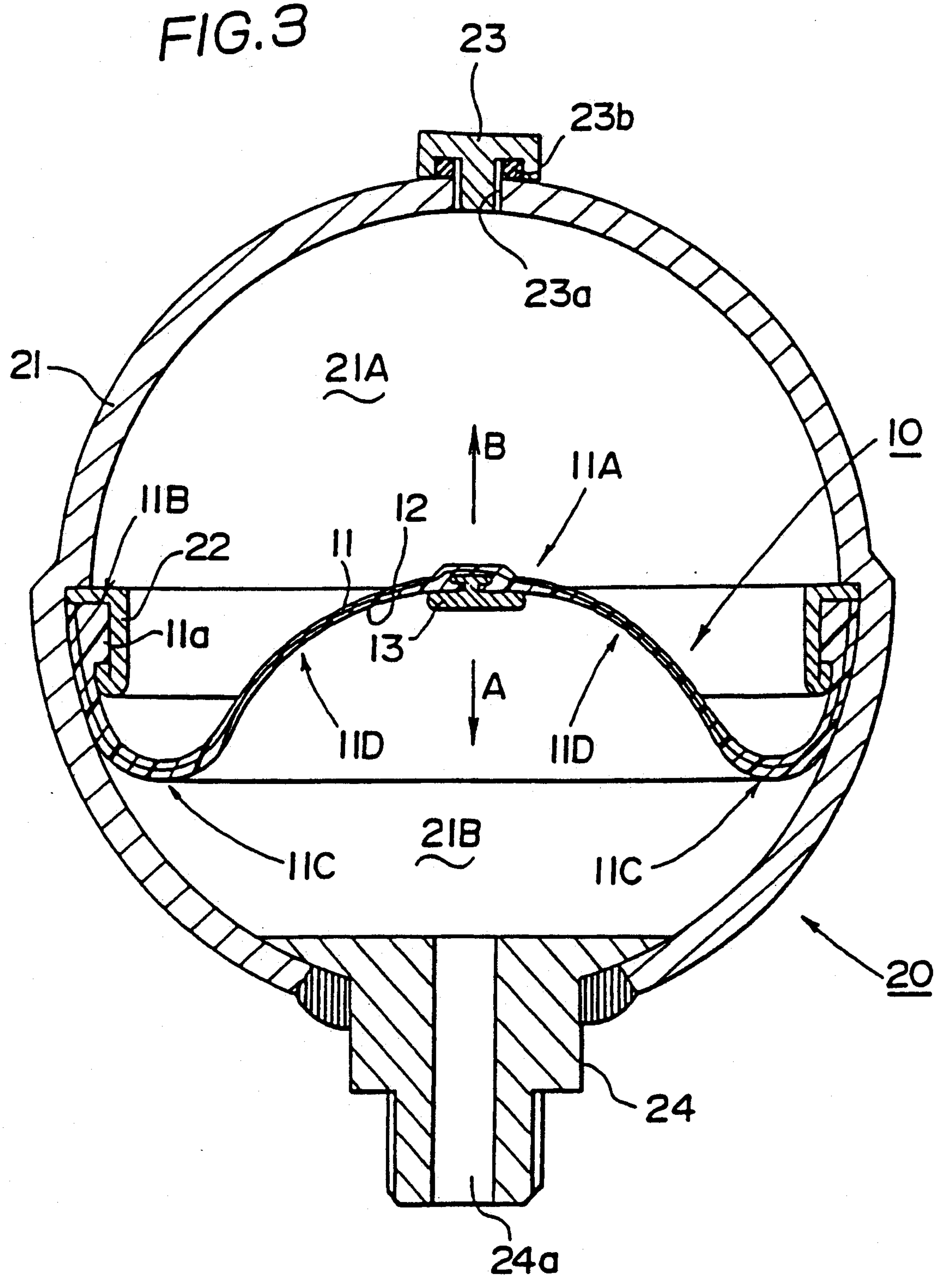
FIG. 3 is a cross sectional view showing an accumulator equipped with the bladder shown in FIG. 1.

FIGS. 1 to 3 show a first embodiment of the present invention. A bladder 10 for an accumulator according to this invention includes an elastic material layer 11, a gas-barrier layer 12 laminated thereon and a poppet 13 attached thereto. The elastic material layer 11 is made of a suitable elastic material such as rubber. The gas-barrier layer 12 is laminated on the entire inner surface of the elastic material layer 11. The poppet 13 is arranged on an outer surface of a central portion 11A of the elastic material layer 11 so as to face a liquid chamber 21B which will be later described.

The elastic material layer 11 has a thick fitting portion 11*a* made of rubber or any other elastic material so as to ensure a seal between an inner surface of a shell 21 and an attaching element 22 when the bladder is attached to the shell 21 by means of the attaching element 22. The thick fitting portion 11*a* is positioned at an inner surface of its peripheral edge portion 11B so as to face toward a gas chamber 21A.

A curved inversion area 11C of the elastic material layer 11 is positioned between its central portion 11A and its peripheral edge portion 11B. The elastic material layer 11 has such a predetermined thickness t that it can be prevented from expanding at an outer surface of the curved inversion area 11C beyond the breaking expansion limit of the gas-barrier layer 12. That is, an intermediate portion 11D which is usually positioned between the central portion 11A and the curved inversion area 11C has a reduced thickness. The reduced thickness of the intermediate portion 11D preferably ranges from the central portion 11A or the vicinity of the poppet 13 to the vicinity of an inner inversion end R1 of the curved inversion area 11C, because the stress due to the expansion of the elastic material layer 11 can be prevented from lumping in a specific portion, for instance, the vicinity of an outer inversion end Ro of the curved inversion area 11C or the vicinity of the inner inversion end R1. It is preferable that both ends of the thickness-reduced intermediate portion 11D gradually increase in thickness so as to be smoothly connected with the curved inversion area 11C and the central portion 11A. The degree of reducing the thickness t of the elastic material layer 11 is determined in such a manner that the elastic material layer 11 does not expand beyond the breaking expansion limit of the gas-barrier layer 12 when the stress in the curved inversion portion 11C becomes a maximum and depends on the materials and/or conditions to be employed for the elastic material layer 11 and the gas-barrier layer 12.

The curved inversion portion 11C is usually an annular portion which projects into the liquid chamber 21B when the bladder 10 is in non-load condition.

The gas-barrier layer 12 is made of a reinforcing material such as a woven sheet or non-woven sheet and a resin layer or a metal foil having a low gas-permeability which is formed on at least one surface of the reinforcing sheet as a gas shielding film although not shown. The resin layer may be made of polyvinyl alcohol type resin, polyvinyl fluoride type resin or vinylidene chloride type resin. Although the gas-barrier layer 12 is usually composed of at least one reinforcing sheet and at least one gas-shielding film in combination, the reinforcing sheet can be omitted if desired. In addition, in order to improve non-gas permeability, the gas-barrier layer can be made in such a condition that a plurality of layers are laminated. In case of polyvinyl alcohol type resin, polyol type plasticizer is preferably contained therein at the rate of 10% to 50% by weight so that the flexibility in cold conditions can be improved. For the purpose of protecting it against fluids such as brake fluids or mineral oils, one side or both sides of the gas-barrier film can be laminated with ethylene-vinyl alcohol copolymer, polyvinyl fluoride, hexafluoropylene, tetrafluroethylene or the like. A partly saponified polyvinyl alcohol type film has a good durability against fluids and in particular brake fluids and mineral oils. It can protect a polyvinyl alcohol layer. The plasticizer contained in the polyvinyl alcohol can be prevented from discharging from the polyvinyl alcohol layer into the liquid chamber and the gas chamber by means of the partly saponified polyvinyl alcohol type film.

An accumulator 20 has the gas chamber 21A and the liquid chamber 21B divided by the bladder 10 in the shell 21. The outer periphery 11B of the bladder 10 is set on the inner surface of the shell 21, and then the attaching element 22 is set on the elastic fitting portion **11*a* of the elastic material layer 11 in such a manner that the latter can be pressed onto the inner surface of the shell 21 as best shown in FIG. 3. After a such as nitrogen gas is supplied at a desired pressure into the gas chamber 21A in the shell 21 through an inlet port 23*a*, the inlet port 23*a* is closed by a closing element 23 and a seal element 23*b* so that the gas chamber 21A** is maintained in a sealed condition.

An oil port element 24 is fixed to the liquid chamber 21B of the shell 21 so as to be selectively open or closed at its inner opening side by means of the poppet 13 which is fixed to the center of the bladder 10. The oil port element 24 has a liquid introducing hole **24*a* through which the liquid chamber 21B is connected to a liquid source (not shown) placed outside of the shell 21. A desired volume of liquid is supplied into the liquid chamber 21B from the liquid source by way of the hole 24*a* of the oil port element 24** so as to depend on a pressure in the liquid source.

The operation of the first embodiment will be explained.

In case the bladder 10 is in non-load condition, the central portion 11A is inverted at the curved inversion area 11C so as to protrude into the gas chamber 21A in the extending direction of the peripheral edge portion 11B as shown in FIGS. 1 and 2.

At this stage, the elastic material layer 11 is in non-load condition at both inner and outer surface portions thereof within the curved inversion portion 11C. Thus, no substantial stress is created. The elastic material layer 11 is not deformed.

If the liquid pressure in the liquid source decreases, then the central portion 11A of the bladder 10 gradually moves into the liquid chamber 21B in the discharging direction designated by the arrow A in FIG. 3 until the liquid pressure in the liquid chamber 21B becomes equal to the gas pressure in the gas chamber 21A.

At this stage, the curved inversion area 11C is deformed in such a way that the inner surface portion of the elastic material layer 11 is expanded while the outer surface portion thereof is contracted. Also, the central portion 11A moves toward the inversion point or points of the curved inversion area 11C. As the thickness t of the elastic material layer 11 is decreased at the intermediate portion 11D so as to have a small rigidity, the outer surface portion of the elastic material layer 11 can be prevented from expanding beyond the breaking expansion limit of the gas-barrier layer 12. In addition, buckling of the gas-barrier layer 12 can be avoided.

If the liquid pressure in the liquid source increases, the central portion 11A of the bladder 10 gradually moves into the gas chamber 21A in the suction direction designated by the arrow B in FIG. 3 until the gas pressure in the gas chamber 21A becomes equal to the liquid pressure in the liquid chamber 21B.

At this stage, the curved inversion area 11C is deformed in such a way that the inner surface portion of the elastic material layer 11 is contracted while the outer surface portion thereof is expanded. Also, the inversion points of the curved inversion area 11C move in the general direction of extension of the peripheral portion 11B. As the thickness t of the elastic material layer 11 is decreased at the intermediate portion 11D so as to have a small rigidity, the outer surface portion of the elastic material layer 11 can be prevented from expanding beyond the breaking expansion limit of the gas-barrier layer 12. In addition, buckling of the gas-barrier layer 12 can be avoided.

Therefore, in a bladder for an accumulator according to this invention, when the central portion 11A repeatedly moves in relation to the oil port element 24 in response to the liquid pressure changing in the liquid source, any stress can be prevented from lumping in a specific portion in a radial direction. In addition, buckling of the gas-barrier layer 12 can be avoided at the curved inversion area 11C.

Accordingly, even if the gas-barrier layer 12 is made of a resin material having a small elasticity, the bladder 10 can properly response to the liquid pressure changing in the liquid source. Thus, it can have an excellent durability and a long life time.

THE SECOND EMBODIMENT

Figure 4:
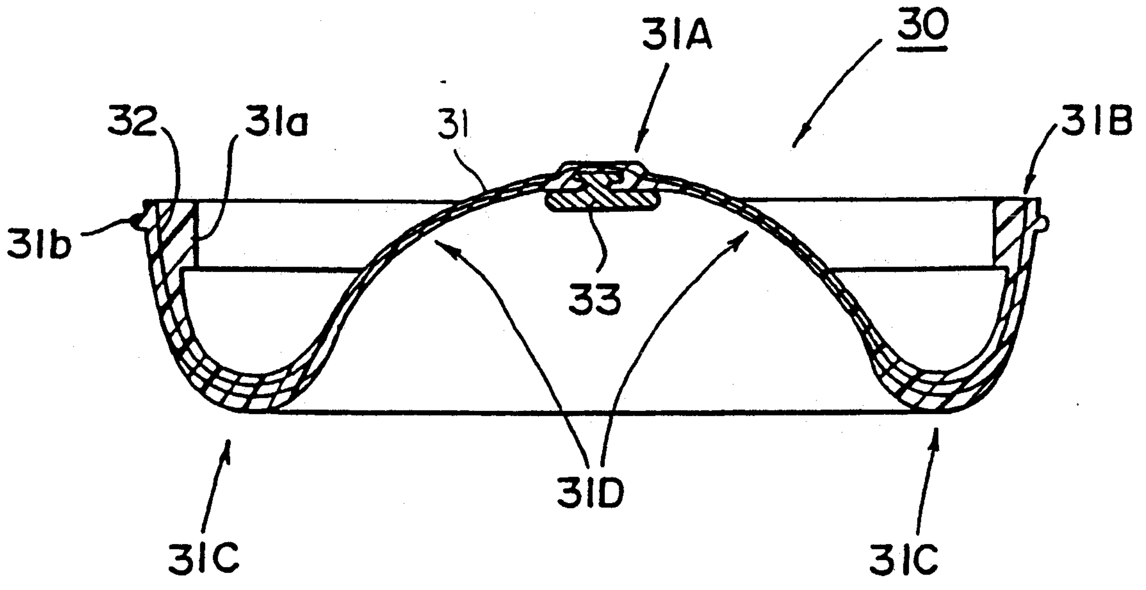
FIG. 4 is a cross sectional view showing a bladder for an accumulator according to a second embodiment of the present invention.
Figure 5:
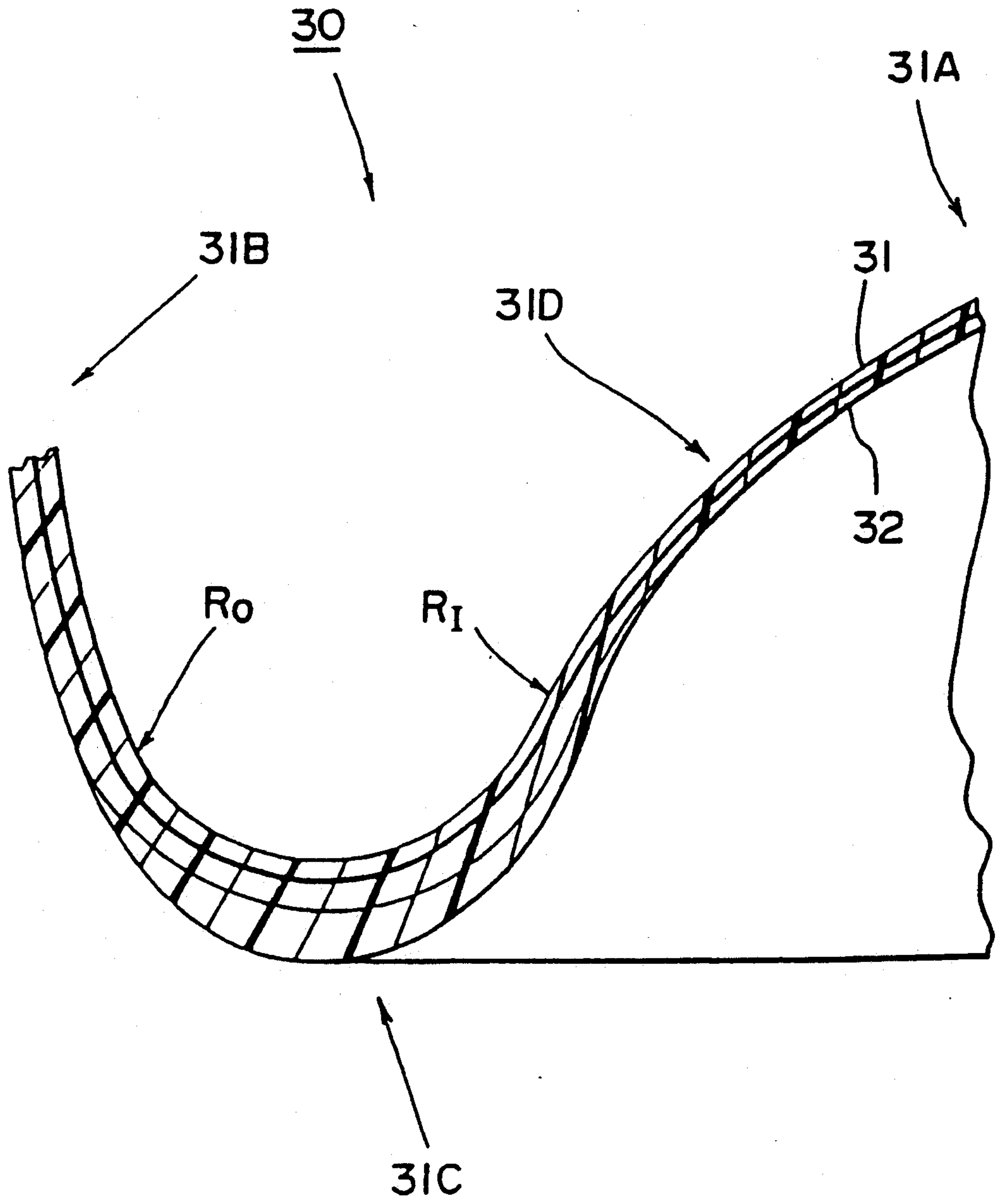
FIG. 5 is an cross sectional enlarged view showing a portion of the bladder shown in FIG. 4.
Figure 6:
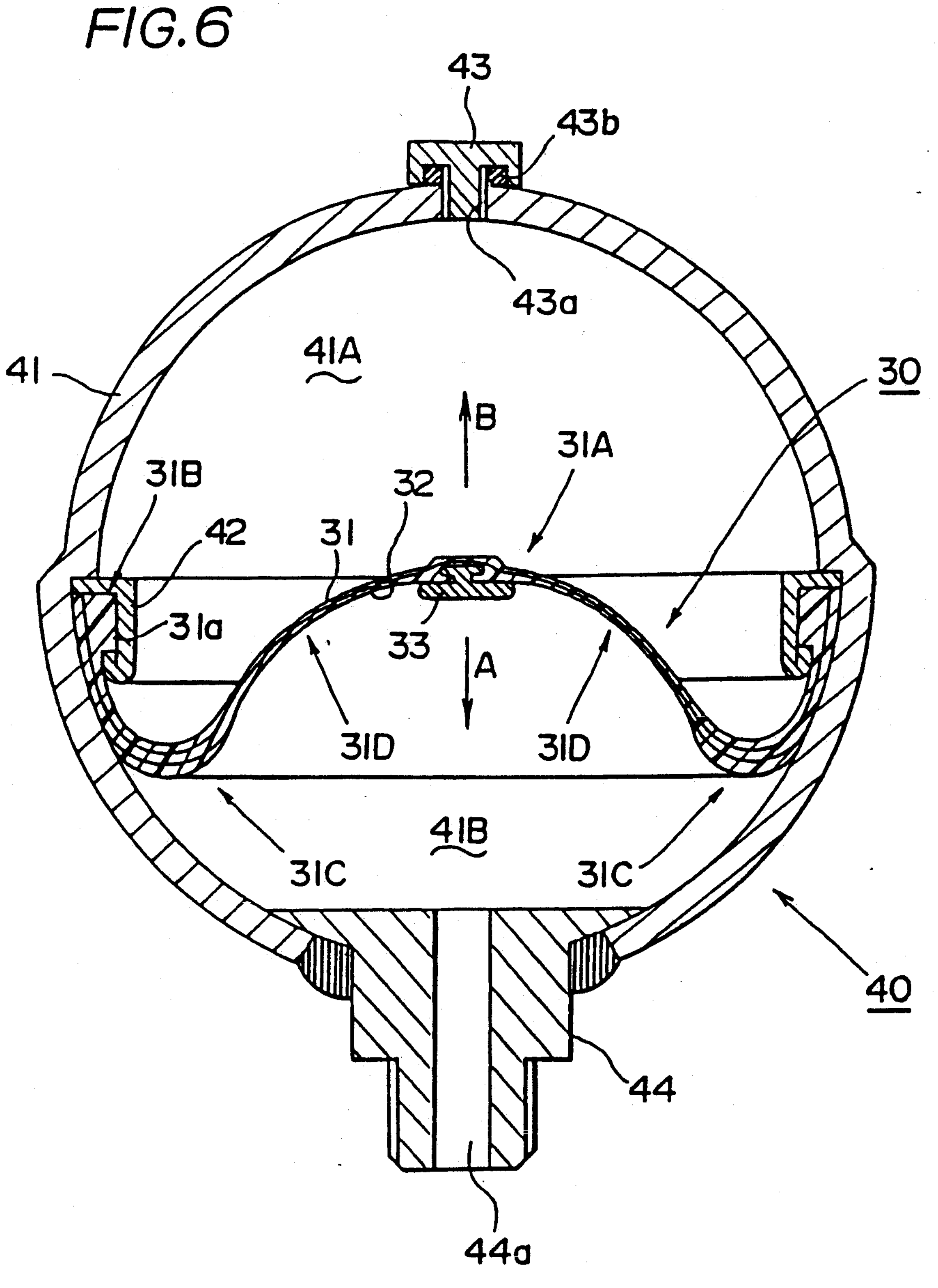
FIG. 6 is a cross sectional view showing an accumulator equipped with the bladder shown in FIG. 4.

FIGS. 4 to 6 show a second embodiment of the present invention. A bladder 30 for an accumulator includes an elastic material layer 31, a gas-barrier layer 32 an a poppet 33. The elastic material layer 31 is made of a suitable elastic material such as a rubber. The gas barrier layer 32 is laminated on the inside of the elastic material layer 31. The poppet 33 is attached on a central portion 31A of the elastic material layer 31 so as to face a liquid chamber 41B.

The elastic material layer 31 has a thick fitting portion 31*a* made of a rubber or any other elastic material so as to ensure a seal between an inner surface of a shell 31 and an attaching element 42 when the bladder is attached to the shell 41 by means of the attaching element 42. The fitting portion 31*a* is positioned at its peripheral edge portion 31B so as to face toward a gas chamber 41A.

A curved inversion area 31C of the elastic material layer 31 is positioned between its central portion 31A and its peripheral edge portion 31B. The elastic material layer 31 has such a predetermined thickness t that it can be prevented from expanding at an outer surface of the curved inversion area 31C beyond the breaking expansion limit of the gas-barrier layer 32. That is, an intermediate portion 31D is placed between the central portion 31A and the curved inversion area 31C and has a reduced thickness. The reduced thickness of the intermediate portion 31D preferably ranges from the central portion 31A or the vicinity of the poppet 13 to the vicinity of an inner inversion end $R_I$ of the inversion area 31C because the stress due to the expansion of the elastic material layer 31 can be prevented from lumping in a specific portion, for instance, the vicinity of an outer inversion end $R_O$ or the vicinity of the inner inversion end $R_I$. It is preferable that both ends of the reduced-thickness intermediate portion 31D gradually increase in thickness so as to be smoothly connected with the curved inversion area 31C and the central portion 31A. The degree of reducing the thickness t of the elastic material layer 31D is determined in such a manner that the elastic material layer 31 does not expand beyond the breaking expansion limit of the gas-barrier layer 32 when the stress in the curved inversion portion 31C becomes maximum and depends on employed materials and/or conditions of the elastic material layer 31 and the gas-barrier layer 32.

The curved inversion portion 31C is usually an annular portion which projects into the liquid chamber 41B when the bladder 30 is in no load condition.

As best shown in FIG. 5, the elastic material layer 31 increases in thickness at or in the vicinity of the curved inversion area 31C. Preferably, the increased thickness t of the elastic material layer 31 ranges from an inner point positioned slightly beyond the inner inversion point $R_I$ to an outer point positioned slightly beyond the outer inversion point $R_O$ in order that the stress due to the expansion of the elastic material layer 31 can be prevented from lumping in a specific portion, for instance, the vicinity of an outer inversion end $R_O$ or the vicinity of the inner inversion point $R_I$. It is preferable that both ends of the thickness-increased portion gradually decrease in thickness. The degree of increasing the thickness t of the elastic material layer 31 is determined in such a manner that the elastic material layer 31 does not expand beyond the breaking expansion limit of the gas-barrier layer 32 when the stress in the curved inversion portion 31C becomes maximum. It depends on employed materials and/or conditions of the elastic material layer 31 and the gas-barrier layer 32.

The gas-barrier layer 32 is made of a reinforcing material such as a woven sheet or non-woven sheet and a resin layer or a metal foil having a low gas-permeability which is formed on at least one surface of the reinforcing sheet as a gas shielding film although not shown. The resin layer may be made of polyvinyl alcohol type resin, polyvinyl fluoride type resin or vinylidene chloride type resin. Although the gas-barrier layer 32 is usually composed of at least one reinforcing sheet and at least one gas-shielding film, the reinforcing sheet can be omitted if desired.

An accumulator 40 has the gas chamber 41A and the liquid chamber 41B divided by the bladder 30 in the shell 41. The outer periphery 31B of the bladder 30 is set on the inner surface of the shell 41, and then the attaching element 42 is set on the fitting portion 31*a* of the elastic material layer 31 in such a manner that the latter is pressed toward the inner surface of the shell 41 as best shown in FIG. 6.

After gas, at an appropriate pressure such as nitrogen gas is supplied into the gas, chamber 41A in the shell 41 through an inlet port 43*a*, the inlet port 43*a* is closed by a closing element 43 and a seal element 43*b* so that the gas chamber 41A is in a sealed condition.

An oil port element 44 is attached to the liquid chamber 41B of the shell 41 so as to be selectively open or closed at its inner opening side by the poppet 33 fixed to the bladder 30. The oil port element 44 has a liquid introducing hole 44*a* through which the liquid chamber 41B is connected to a liquid source (not shown) placed outside of the shell 41. A desired volume of liquid is supplied into the liquid chamber 41B from the liquid source by way of the hole 44*a* of the oil port element 44 according to the pressures in the liquid source.

The operation of the second embodiment will be explained, referring to FIGS. 4 to 6.

When case the bladder 30 is in non-load condition, the central portion 31A is inverted at the curved inversion area 31C so as to protrude into the gas chamber 41A in the extending direction of the peripheral edge portion 31B.

At this stage, the elastic material layer 31 is in non load condition at both inner and outer surfaces thereof within the curved inversion portion 31C. Thus, no stress is created. The elastic material layer 31 is not deformed.

If the liquid pressure in the liquid source decreases, then the central portion 31A of the bladder 30 gradually moves into the liquid chamber 41B in the discharging direction designated by the arrow A in FIG. 6 until the liquid pressure in the liquid chamber 41B becomes equal to the gas pressure in the gas chamber 41A.

At this stage, the curved inversion area 31C is deformed in such a way that the inner surface portion of the elastic material layer 31 is expanded while the outer surface portion thereof is contracted. Also, the central portion 31A moves toward the curved inversion area 31C. Because the thickness t of the elastic material layer 31 is decreased at the intermediate portion 31D so as to have a small rigidity and then increased at its outer surface side in the vicinity of the curved inversion area 31C, the outer surface portion of the elastic material layer 31 can be prevented from expanding beyond the breaking expansion limit of the gas-barrier layer 32. It is more advantageous than that of the first embodiment.

As the increased thickness range extends from the inner point slightly beyond the inner inversion point $R_I$ to the outer point slightly beyond the outer inversion point $R_O$, the stress can be prevented from lumping in a specific area such as the inner inversion point $R_I$ and the outer inversion point $R_O$. In addition, buckling of the gas-barrier layer 32 can be avoided. Such advantages of the second embodiment are more excellent than those of the first embodiment.

If the liquid pressure in the liquid source increases, the central portion 31A of the bladder 30 gradually moves into the gas chamber 41A in the suction direction designated by the arrow B in FIG. 6 until the gas pressure in the gas chamber 41A becomes equal to the liquid pressure in the liquid chamber 41B.

At this stage, the curved inversion area 31C is deformed in such a way that the inner surface portion of the elastic material layer 31 is contracted while the outer surface portion thereof is expanded. Also, the inversion point of the curved inversion area 31C moves toward the direction of extension of the peripheral portion 31B. Because the thickness t of the elastic material layer 31 is decreased at the intermediate portion 31D so as to have a small rigidity and then increased at its outer surface side in the vicinity of the curved inversion area 31C, the outer surface portion of the elastic material layer 31 can be prevented from expanding beyond the breaking expansion limit of the gas-barrier layer 32. It is more advantageous than that of the first embodiment. As the increased thickness range extends from the inner point slightly beyond the inner inversion point $R_I$ to the outer point slightly beyond the outer inversion point $R_O$, the stress can be prevented from lumping in a specific area such as the inner inversion point $R_I$ and the outer inversion point $R_O$. In addition, buckling of the gas-barrier layer 32 can be avoided. Such advantages of the second embodiment are more excellent than those of the first embodiment.

Therefore, in the bladder 30 for an accumulator, when the central portion 31A repeatedly moves in relation to the oil port element 44 in response to the liquid pressure changing in the liquid source, the stress can be prevented from lumping in a specific portion in a radial direction. In addition, buckling of the gas-barrier layer 32 can be avoided at the curved inversion area 31C. Accordingly, even if the gas-barrier layer 32 is made of a resin material having a small elasticity, the bladder 30 can properly respond to the liquid pressure changes in the liquid source. Thus, it can have an excellent durability and a long life time. Such advantages of the second embodiment are more excellent than those of the first embodiment.

THE THIRD EMBODIMENT

Figure 7:
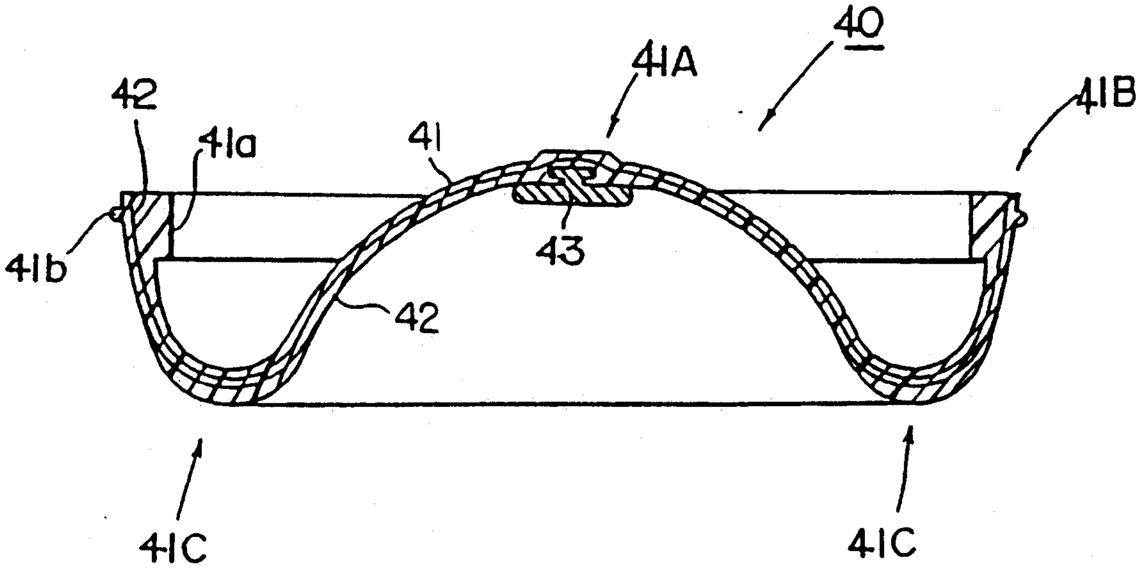
FIG. 7 is a sectional view showing a bladder for an accumulator according to a third embodiment of the present invention.
Figure 8:
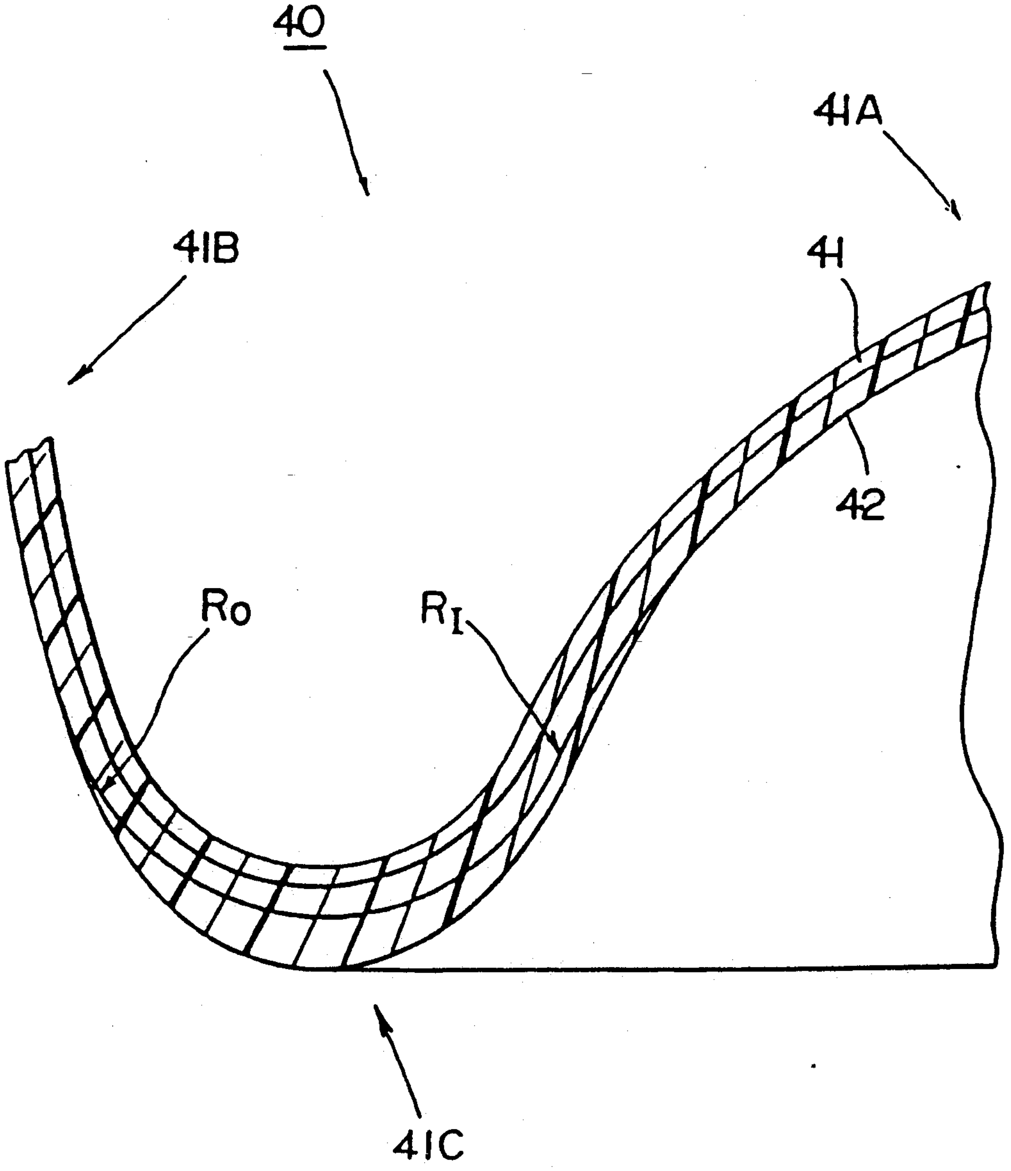
FIG. 8 is an enlarged cross sectional view showing a portion of the bladder shown in FIG. 7.
Figure 9:
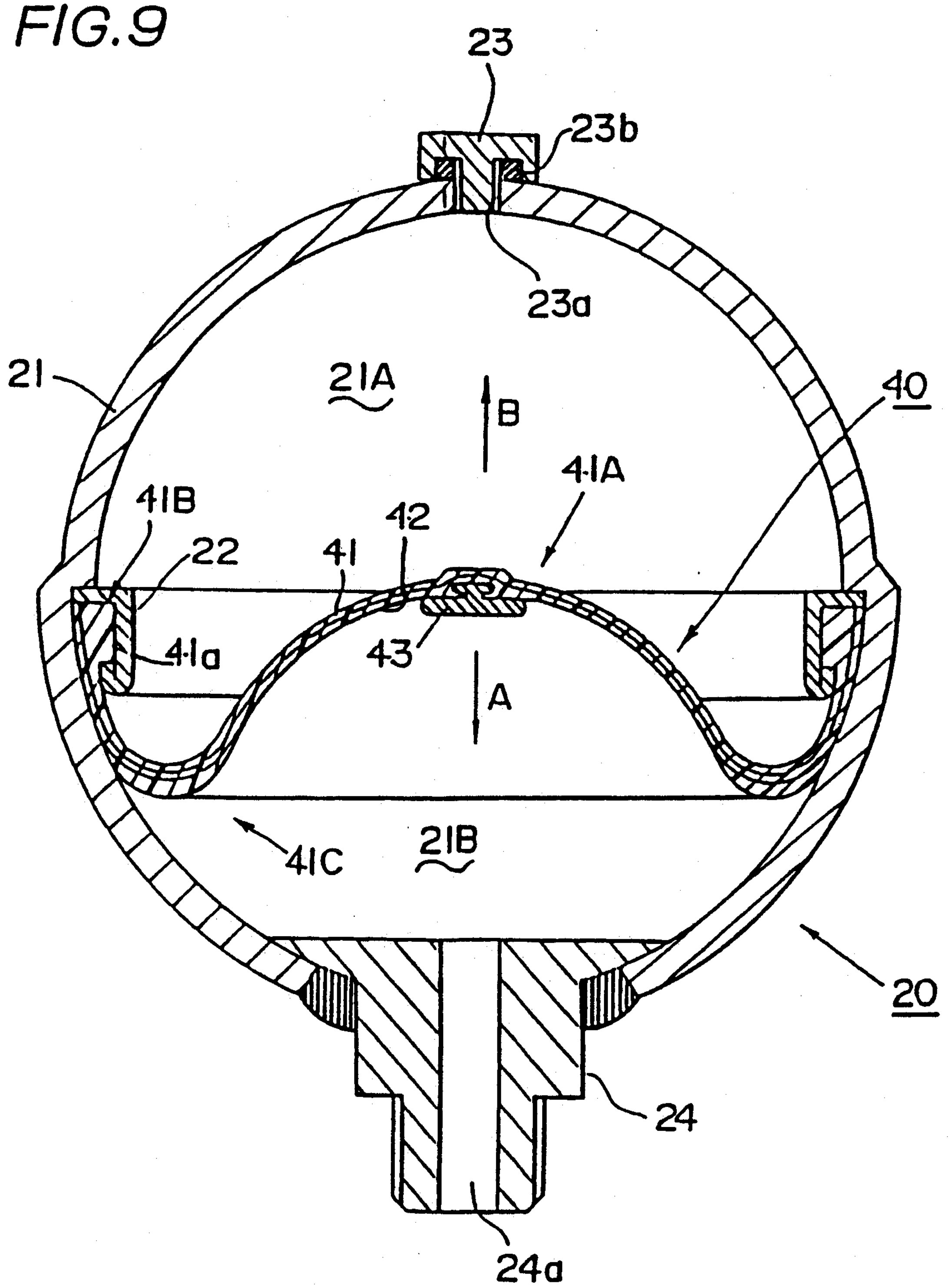
FIG. 9 is a cross sectional view showing an accumulator equipped with the bladder shown in FIG. 7.

FIGS. 7 to 9 show a third embodiment of the present invention. A bladder 40 for an accumulator includes an elastic material layer 41, a gas-barrier layer 42 and a poppet 43. The elastic material layer 41 is made of a suitable elastic material such as a rubber. The gas barrier layer 42 is laminated on the inside or surface of the elastic material layer 41. The poppet 43 is arranged on an outer surface of a central portion 41A of the elastic material layer 41 so as to face a liquid chamber 21B which will be later described.

The elastic material layer 41 has a thick fitting portion 41*a* made of a rubber or any other elastic material so as to ensure a seal between an inner surface of a shell 21 and an attaching element 22 when the bladder is attached to the shell 21 by means of the attaching element 22. The thick fitting portion 41*a* is positioned at an inner surface of its peripheral edge portion 41B so as to face toward a gas chamber 21A.

A curved inversion area 41C of the elastic material layer 41 is positioned between its central portion 41A and its peripheral edge portion 41B.

The elastic material layer 41 has such a predetermined thickness t that it can be prevented from expanding at an outer surface of the curved inversion area 41C beyond the breaking expansion limit of the gas-barrier layer 42, by increasing the thickness of the curved inversion area 41C at its outer surface portion between the central portion 41A and the peripheral edge portion 41B. The increased thickness range of the elastic material layer 41 preferably extends from an inner point slightly beyond the inner inversion point $R_I$ to an outer point slightly beyond the outer inversion point $R_O$ because the stress due to the expansion of the elastic material layer 41 can be prevented from lumping in a specific portion, for instance, the vicinity of the outer inversion point Ro or the vicinity of the inner inversion point $R_I$. It is preferable that both ends of the thickness-increased portion gradually decrease in thickness.

The curved inversion portion 41C is an annular portion which projects into the liquid chamber 21B when the bladder 40 is in non-load condition.

The gas-barrier layer 42 is made of a reinforcing material such as a woven sheet or non-woven sheet and a resin layer or a metal foil having a low gas-permeability which is formed on at least one surface of the reinforcing sheet as a gas shielding film although not shown. The resin layer may be made of polyvinyl alcohol type resin, polyvinyl fluoride type resin or vinylidene chloride type resin. Although the gas-barrier layer 42 is usually composed of at least one reinforcing sheet and at least one gas-shielding film, the reinforcing sheet can be omitted if desired.

Like in the first embodiment, the accumulator 20 has the gas chamber 21A and the liquid chamber 21B divided by the bladder 40 in the shell 21. The outer periphery 41B of the bladder 40 is set on the inner surface of the shell 21, and then the attaching element 22 is set on the elastic fitting portion 41*a* of the elastic material layer 41 in such a manner that the latter can be pressed onto the inner surface of the shell 21 as best shown in FIG. 9.

After gas such as nitrogen is supplied at the desired pressure into the gas chamber 21A in the shell 21 through the inlet port 23*a*, the inlet port 23*a* is closed by the closing element 23 and the seal element 23*b* so that the gas chamber 21A is held in a sealed condition.

The oil port element 24 is attached to the liquid chamber 21B of the shell 21 so as to be selectively open or closed at its inner opening side by the poppet 43 fixed to the bladder 40. Through the oil introducing hole 44*a*, the liquid chamber 21B is connected to a liquid source (not shown) placed outside of the shell 21. A desired volume of liquid is supplied into the liquid chamber 21B from the liquid source by way of the hole 24*a* of the oil port element 24 according to the pressures in the liquid source.

Referring now to FIGS. 7 to 9, the operation of the third embodiment will be explained.

When the bladder 40 is in no load condition, the central portion 41A is inverted at the curved inversion area 41C so as to protrude into the gas chamber 21A in the extending direction of the peripheral edge portion 41B as shown in FIG. 9.

At this stage, the elastic material layer 41 is in no load condition at both inner and outer surfaces thereof within the curved inversion portion 41C. Thus, no stress is created and the elastic material layer 41 is not deformed.

If the liquid pressure in the liquid source decreases, then the central portion 41A of the bladder 40 gradually moves into the liquid chamber 21B in the discharging direction designated by the arrow A in FIG. 9 until the liquid pressure in the liquid chamber 21B becomes equal to the gas pressure in the gas chamber 21A.

At this stage, the curved inversion area 41C is deformed in such a way that the inner surface portion of the elastic material layer 41 is expanded while the outer surface portion thereof is contracted. Also, the central portion 41A moves toward the inversion points of the curved inversion area 41C. As the thickness t of the elastic material layer 41 is increased at the outer surface portion thereof, the outer surface portion of the elastic material layer 41 can be prevented from expanding beyond the breaking expansion limit of the gas-barrier layer 42. Because the increased thickness range of the elastic material layer 41 at its outer surface side extends from the inner point slightly beyond the inner inversion point $R_I$ to the outer point slightly beyond the outer inversion point $R_O$, the stress can be prevented from lumping in a specific area in a radial direction such as the inner inversion point $R_I$ and the outer inversion point $R_O$. In addition, buckling of the gas-barrier layer 42 can be avoided.

If the liquid pressure in the liquid source increases, the central portion 41A of the bladder 40 gradually moves into the gas chamber 21A in the suction direction designated by the arrow B in FIG. 9 until the gas pressure in the gas chamber 21A becomes equal to the liquid pressure in the liquid chamber 21B.

At this stage, the curved inversion area 41C is deformed in such a way that the inner surface portion of the elastic material layer 41 is contracted while the outer surface portion thereof is expanded. Also, the inversion point of the curved inversion portion 41C move toward the general direction of extension of the peripheral portion 41B. As the thickness t of the elastic material layer 41 is increased at the outer surface portion thereof, the outer surface portion of the elastic material layer 41 can be prevented from expanding beyond the breaking expansion limit of the gas-barrier layer 42. Also, because the increased thickness range of the elastic material layer 41 at its outer surface side extends from the inner point slightly beyond the inner inversion point $R_I$ to the outer point slightly beyond the outer inversion point $R_O$, the stress can be prevented from lumping in a specific area in a radius direction such as the inner inversion point $R_I$ and the outer inversion point $R_O$. In addition, buckling of the gas-barrier layer 42 can be avoided.

Therefore, in the bladder 40, when the central portion 41A repeatedly moves in relation to the oil port element 24 in response to the liquid pressure changing in the liquid source, the stress can be prevented from lumping in a specific portion in a radial direction. In addition, buckling of the gas-barrier layer 42 can be avoided at the curved inversion area 41C.

Accordingly, even if the gas-barrier layer 42 is made of a resin material having a small elasticity, the bladder 40 can properly respond to the liquid pressure changing in the liquid source. Thus, it can have an excellent durability and a long life time.

It will be clear from the drawings that the relative thicknesses of the intermediate and curved inversion portions are such that the curved inversion portion is approximately two or three times that of the intermediate portion.

The present invention may be embodied in other specific forms without departing from the spirit or essential features thereof. The illustrated embodiments are therefore to be considered in all respects as illustrative and not restrictive. All changes which come within the meaning and range of equivalency of the claims are intended to be embraced in the present invention.

What is claimed is:

1. A bladder for use in the interior of a hollow shell of an accumulator, comprising:
   - an elastic material layer having a central portion and a radially outer peripheral edge portion;
   - a gas-barrier layer laminated on said elastic material layer;
   - an elastic fitting portion formed at said peripheral edge portion of said elastic material layer to be pressed radially outwardly toward the inner wall of said shell in an assembled position;
   - an attaching means for attaching said fitting portion to said inner wall of said shell in said assembled position wherein said elastic material layer faces a first fluid section in said shell and said gas-barrier layer faces a second fluid section of said shell;
   - an intermediate portion proximate said central portion and connected thereto, said central portion and intermediate portion having a convex/concave cross-sectional shape with the convex side facing said first fluid section and the concave side facing said second fluid section; and
   - a curved inversion portion having a convex/concave cross-sectional shape, with the convex side facing said second fluid section and said concave side facing said first fluid section, connected to and disposed between said intermediate portion and said peripheral edge portion, the thickness of said bladder between said central portion and said outer peripheral portion varying so that said intermediate portion comprises a thinner portion for reducing rigidity thereof and said curved inversion portion is substantially thicker than said intermediate portion in an amount and to a degree so that stress due to expansion of said elastic material layer is prevented from lumping in said curved inversion portion and said elastic material layer is prevented from expanding at an outer surface thereof facing said first fluid section beyond a breaking expansion limit of said gas-barrier layer.

2. A bladder as claimed in claim 1, wherein:
   - said thickness of said curved inversion portion is at least twice said thickness of said intermediate portion.

3. A bladder as claimed in claim 2, wherein:
   - said thickness of said curved inversion portion is approximately three times said thickness of said intermediate portion.

4. A bladder as claimed in claim 3, wherein:
   - said thickness of said intermediate portion gradually increases proximate the ends thereof where said intermediate portion is connected to said central portion and said curved inversion portion.

5. A bladder as claimed in claim 2, wherein:

said thickness of said intermediate portion gradually increases proximate the ends thereof where said intermediate portion is connected to said central portion and said curved inversion portion.

6. A bladder as claimed in claim 1, wherein:

said thickness of said intermediate portion gradually increases proximate the ends thereof where said intermediate portion is connected to said central portion and said curved inversion portion.

7. An accumulator comprising:

a hollow shell;

a bladder within said shell comprising;

an elastic material layer having a central portion and a radially outer peripheral edge portion, a gas-barrier layer laminated on said elastic material layer, an elastic fitting portion formed at said peripheral edge portion of said elastic material layer to be pressed radially outwardly toward the inner wall of said shell in an assembled position, an attaching means for attaching said fitted portion to said inner wall of said shell in said assembled position wherein said elastic material layer faces a first fluid section in said shell and said gas-barrier layer faces a second fluid section in said shell, an intermediate portion proximate said central portion and connected thereto, said central portion and intermediate portion having a convex/concave cross-sectional shape with the convex side facing said first fluid section and the concave side facing said second fluid section, and a curved inversion portion having a convex/concave cross-sectional shape, with the convex side facing said second fluid section and said concave side facing said first fluid section, connected to and disposed between said intermediate portion and said peripheral edge portion, the thickness of said bladder between said central portion and said outer peripheral portion varying so that said intermediate portion comprises a thinner portion for reducing rigidity thereof and said curved inversion portion is substantially thicker than said intermediate portion in an amount and to a degree so that stress due to expansion of said elastic material layer is prevented from lumping in said curved inversion portion and said elastic material layer is prevented from expanding at an outer surface thereof facing said first fluid section beyond a breaking expansion limit of said gas-barrier layer, said thickness of said curved inversion portion being at least twice said thickness of said intermediate portion; and a poppet attached to said central portion on the side thereof facing said second fluid section.

8. An accumulator as claimed in claim 7, and further comprising:

an inner inversion point on said curved inversion portion adjacent said connection of said curved inversion portion with said intermediate portion; and an outer inversion point on said curved inversion portion adjacent said connection between said curved inversion portion and said outer peripheral edge portion, said greater thickness of said curved inversion portion extending substantially between said inner and outer inversion points.

9. An accumulator as claimed in claim 7, wherein:

said thickness of said curved inversion portion gradually decreases at said connections thereof to said intermediate portion and said outer peripheral edge portion.

* * * * *